United States Patent [19]
Burchett et al.

[11] Patent Number: 5,922,754
[45] Date of Patent: Jul. 13, 1999

[54] PHARMACEUTICAL COMPOSITIONS CONTAINING PACLITAXEL

[75] Inventors: Mark K. Burchett, Waukegan; Cynthia A. Coddington, Gurnee; Rajagopalan Raghavan, Grayslake; Earl R. Speicher, Buffalo Grove, all of Ill.

[73] Assignee: Abbott Laboratories, Abbott Park, Ill.

[21] Appl. No.: 09/165,930

[22] Filed: Oct. 2, 1998

[51] Int. Cl.$^6$ .................................................. A61K 31/335
[52] U.S. Cl. ............................................................ 514/449
[58] Field of Search ............................................... 514/449

[56] References Cited

U.S. PATENT DOCUMENTS

| | | | |
|---|---|---|---|
| 5,504,102 | 4/1996 | Agharkar et al. | 514/449 |
| 5,681,846 | 10/1997 | Trissel | 514/449 |
| 5,733,888 | 3/1998 | Carver et al. | 514/449 |

*Primary Examiner*—Raymond Henley, III
*Attorney, Agent, or Firm*—Gregory W. Steele

[57] ABSTRACT

The present invention provides novel paclitaxel formulations which may be terminally sterilized and show long term stability in water containing admixtures.

16 Claims, No Drawings

PHARMACEUTICAL COMPOSITIONS CONTAINING PACLITAXEL

FIELD OF THE INVENTION

The present invention is directed to a pharmaceutical composition that contains paclitaxel.

BACKGROUND OF THE INVENTION

Pharmaceutical compositions usually require a suitable solvent system to solubilize or disperse the active drug component for administration to a patient. The solvent must be capable of solubilizing or dispersing a therapeutically effective amount of the active component and must be non-toxic to the patient.

Many such compositions containing paclitaxel are known but are not stable for long periods of time. U.S. Pat. No. 5,504,102 is directed to a stabilized formulation of paclitaxel that contains Cremophor EL, a condensation product of castor oil and ethylene oxide sold by BASF. U.S. Pat. No. 5,733,888 discloses another stabilized paclitaxel formulation that contains Cremophor EL. However, Cremophor EL has been implicated in causing anaphylactic reactions in some patients. Additionally, when such Cremophor EL containing formulations are admixed with aqueous parenteral infusion fluids such as 0.9% saline, the admixture is stable without precipitation for a short period of time.

Thus, it is an object of the present invention to provide a paclitaxel formulation that is stable for extended periods of time.

It is a further object of the present invention to provide a paclitaxel formulation that does not contain Cremophor EL.

It is still a further object of the present invention to provide a paclitaxel formulation that may be sterilized by terminal sterilization.

It is still a further object of the present invention to provide a paclitaxel formulation that has extended stability when admixed with pharmaceutically acceptable parenteral infusion fluids.

SUMMARY OF THE INVENTION

The present invention is directed to a paclitaxel formulation.

More particularly, the present invention is directed to a pharmaceutical composition comprising paclitaxel, an acid, water and suitable organic solvents. Preferred organic solvents include triacetin, absolute alcohol, and SOLUTOL® HS-15. Preferably the acid is citric acid.

DETAILED DESCRIPTION OF THE INVENTION

The preferred pharmaceutical compositions of the invention are set forth in Table 1.

TABLE 1

| Component | Range Wt % | Preferred Range Wt % | Preferred Composition Wt % (mg/mL) |
|---|---|---|---|
| Anhydrous Citric Acid | 0.2–0.5 | 0.25–0.35 | 0.27 (3.0) |
| Solvent: Triacetin | 5–15 | 8–10 | 9.1 (96.2) |
| Solvent: Glycerol | 16–22 | 18–20 | 19.1 (201.9) |
| Dehydrated Alcohol | 10–50 | 14–16 | 15.1 (159.3) |
| Solutol HS-15 | 40–60 | 45–55 | 47.3 (500) |
| Water | 0–25 | 8–10 | 8.9 (94.2) |
| Paclitaxel | 0.3–0.8 | 0.5–0.7 | 0.57 (6.0) |

The type and amount (per cent) of solvent and alcohol in Table 1 can be varied so long as the total percent of all components does not exceed 100%. For example when 50% wt percent of the formulation comprises paclitaxel, acid, water, and Solutol HS-15, the remaining solvents/alcohol should add up to 50%. Thus the formulations of the invention may be made with a simple component like dehydrated alcohol alone. Alternatively, the composition may contain varying proportions of triacetin and alcohol or triacetin, glycerol and alcohol such that, in each case, the total weight percentages of the components make up the remaining 50% by weight.

Any acid or acidic component whose first aqueous dissociation constant, $k_{a,1}$, (compounds like citric and succinic acids, and the like, having multiple dissociation constants) is equivalent to or greater than $1.8 \times 10^{-6}$, can be used. While anhydrous citric acid is the preferred acid, any other solid acid either in anhydrous or in hydrated form could be used. Mineral acids (e.g., hydrochloric, sulfuric, phosphoric, nitric, etc.), carboxylic acids (e.g., formic, acetic, tartaric, succinic, malic, maleic, oxaloacetic, lactic, hydracrylic, pivalic, benzoic, etc.), strong acids (e.g., methane sulfonic, benzene sulfonic acids, p-tolunesulfonic acid, etc.) may also be employed. Additionally, sugar acids (gluconic, gluceptic, saccharic and the like), amino acids (aspartic, glutamic and the like), acid salts (sodium bisulfate, sodium bisulfite, sodium metabisulfite, monosodium edetate and the like), non-carboxylic acids (e.g., ascorbic, sulfamic) and heterocyclic acid salts (pyridinium hydrochloride, nicotinamide hydrochloride and the like) can also be used.

The compositions of the present invention may also include a solvent for enhancing paclitaxel solubility. Any number of solvents may serve this purpose, however we have found that a combination of triacetin and glycerol is preferred. Suitable other solvents for this purpose include other acetate esters of a similar type derived from glycerin, for example monoacetin and diacetin, can also be used. In addition, esters of glycerin, for instance mono, di, and tri-glyceryl citrates, tartrates, etc. are suitable. Low or medium chain glyceride esters (mono, or di or tri-glyceride) may also be employed provided solubility of paclitaxel can be maintained at a concentration greater than 5 mg/mL. As will be recognized by the skilled person, a number of other excipients suitable for this purpose may be used. Among these are glyceride esters, PEG-hydroxystearate, PEG-hydroxyoleate, alkyl oleates, and such other fatty acid derived PEG esters; esters as benzyl acetate, ethyl benzoate, and benzyl benzoate dimethylacetamide (DMA), dimethylsulfoxide (DMSO), polyvinylpyrrolidone, polysorbate-80, pluronic 60, and the like. Glycerol and triacetin are preferred solvents. If a trihydroxy compound is employed, glycerin is preferred. Propylene glycol and other pharmaceutically acceptable glycols, and substituted glycerols can be readily substituted for glycerin.

The preferred alcohol for use in the compositions of the present invention is ethanol. Any pharmaceutically acceptable alcohol, for example benzyl alcohol, can be used in the compositions of the invention. More than one pharmaceutically acceptable alcohol can be combined in the compositions of the invention.

The compositions of the present invention employ SOLUTOL® HS-15. SOLUTOL® HS-15 is a polyglycol ester of 12-hydroxystearic acid (12-HAS; 70%) and polyethylene glycol (PEG; 30%) and is available from BASF, Ludwigshafen, Germany. Solutol has a hydrophobic component (12-HSA component) and a hydrophilic component (PEG).

In art recognized animal models, the compositions of the present invention provide a level of efficacy similar to, or greater than, that provided by TAXOL® (Bristol Myers Squibb) a commercially available taxane composition.

The invention may be illustrated by the following representative examples.

EXAMPLE 1

10 g of triacetin and 21 mL of alcohol are mixed with about 300 to 360 mg of citric acid until the citric acid is dissolved. 624 mg of paclitaxel is added and dissolved. In a separate container, Solutol is heated to about 40° C. until a clear oily liquid is obtained. Cool to about 30° C. 52 g of liquid Solutol is removed and mixed with 21 g of glycerin. When a homogeneous solution of Solutol and glycerin is obtained, mix the paclitaxel solution prepared in the first step and add 10 mL of water and stir well. Terminally sterilize the resulting formulation, by crimp closing the bottle using appropriate glass container, a Teflon stopper and aluminum seal for crimp-closing the bottle. This formulation is identified as Formulation #3 in Table 2.

EXAMPLE 2

Step 1: Into a 125 mL beaker, add 600 mg of citric acid USP, 4.0 g of Polysorbate-80 USP, 50 g of Triacetin USP and 50 g of Propylene glycol. Stir the mixture until all the citric acid is dissolved.

Step 2: Heat enough Solutol at 40° C. until it liquefies. Transfer 100 g of Solutol into a 200 mL bottle.

Step 3: Transfer the mixture prepared in Step 1 into the bottle prepared in Step 2 and mix the two solutions well, cool to room temperature.

Step 4: Add 1.3 g of paclitaxel into the solution prepared in Step 3 and stir the mixture well until all the paclitaxel is dissolved.

Step 5: Stopper the bottle appropriately and tightly with a Teflon stopper, and crimp close the bottle. Terminally sterilize the bottle at 120° C. for 20 minutes.

EXAMPLE 3

Transfer 52 g of liquefied Solutol, into a 100 mL glass vial. Dissolve 300 mg of anhydrous citric acid in 50 mL of dehydrated alcohol. Transfer 600 mg of paclitaxel into a beaker and dissolve in about 35 mL of ethanol containing citric acid. Transfer the paclitaxel solution thus prepared into the Solutol vial. With the remaining 15 mL of alcohol rinse the beaker multiple times and transfer the paclitaxel quantitatively. Mix the two solutions together until a clear homogeneous solution is obtained.

Adopting procedures similar to those outlined above, a number of paclitaxel formulation solutions were prepared, as shown in Table 2. Thus paclitaxel formulations can be prepared by adding citric acid and paclitaxel at a suitable stage of the preparation of the formulation depending on the nature and relative proportions of the liquid excipients used.

TABLE 2

Examples of Formulation Excipient Composition

| Formulation. No. | Triacetin | Glycerin | Alcohol | Solutol | Water |
|---|---|---|---|---|---|
| 1 | 10 g | 10 g | 10 mL | 30 g | 10 mL (+1.20 g of polysorbate 80 |
| 2 | 7.5 g | 10 g | 7.5 mL | 25.0 g | — |
| 3 | 9 g | 18 g | 18 mL | 46 g | 9 mL |
| 3a | 9 g | 18 g | 22 mL | 46 g | 5 mL |
| 3b | 9 g | 18 g | 18 mL | 46 g | 5 mL (+4 mL PG) |
| 3c | 18 | — | 28 mL | 45 g | 9 mL |
| 4 | 15 g | 15 g | 15 mL | 15 g | 20 mL |
| 4a | 10 g | — | 30 mL | 45 g | 15 mL |
| 4b | 10 g | 10 g | 25 mL | 45 g | 10 mL |

In each formulation of Table 2, the concentration of paclitaxel and citric acid are 6.0 mg/mL and 3.0 mg/mL respectively.

The compositions of the invention may be placed in ampoules, vials or other suitable containers. In order to prevent microbial growth the pharmaceutical formulations of the invention are either aseptically filled by filtration though 0.22 micron filters or are, preferably, terminally sterilized following techniques known in the art, e.g., autoclaving.

Evaluation of Potential Shelf Life of the Compositions of the Invention

Paclitaxel and many taxane analogs degrade in ethanolic solutions to which surfactants like Cremophor have been added. Typically, a shelf life of the formulation is analytically determined after storing the formulation at elevated temperatures for 40° C. over days or months. In the present case, the room temperature stability of the compositions of the invention was estimated by employing the following procedure. Five mL of the formulation was transferred to a 5 mL vials, each vial stoppered with a Teflon-coated stopper and then crimp sealed with aluminum crimps. The sealed vial was then heated either at 60° C. or more preferably at 70° C. for 16 to 24 hours and then cooled to room temperature. The resulting solution was diluted in a suitable diluting solvent and analyzed by high performance liquid chromatography (HPLC). As it is known that paclitaxel will degrade at high temperatures to form baccatin III and side ethyl ester due to the cleavage of the side chain at C-13, as well as other impurities like base-catalyzed epimerization of paclitaxel (e.g., 7-epitaxol), HPLC was used to determine the individual degradants and total of all degradants as a function of time and temperature. All reagents used for chromatography are HPLC grade. The HPLC system utilized a Thermoseparation P 4000 ternary solvent Pump, AS 3000 Autoinjector and Applied Biosystem 785A programmable wavelength detector in sequence with Fisons VG chromatography server data acquisition system connected to a computer containing Fison's Xchrom software for data integration. The analytical column used is Phenomenex, Curosil PFP, 5 micron 25 cm×4.6 mm ID column. A Curosil PFP, 30 mm×4.6 mm guard column is connected in series to the inlet side of the analytical column though a VICCI, Valco instruments automatic column switching device. The gradient mobile phase system consists of 40:60 acetonitrile: –0.1% phosphoric acid mobile phase A and 60:40 acetonitrile: 0.1% phosphoric acid mobile phase B. The gradient conditions between the two mobile phases are adjusted such that the late-eluting 7-epitaxol can be monitored. The guard column is flushed with 50:50 mixture of the above two mobile phases. The flow rate is 1.5 mL per minute through the analytical column, while the flow rate through the second pump used for clean up was maintained at 0.5 mL per minute. An injection volume of 20 microliters was employed. The eluting peaks were monitored at a wavelength of 227 nm. The method involves injection of the suitably diluted sample through the guard column connected to the analytical column. The mobile phase flows through the guard column and then through the analytical column. The mobile phase flow through the two columns in series is maintained for a suitable duration such that all the impurities move from the guard column to the analytical column. After this run time, the guard column connection to the analytical column is cut off and the mobile phase flow continues through the analytical column only. While chromatographic separation is accomplished in the analytical column, the guard column is flushed to remove surfactants via a flushing solution and another pump.

Determination of Potency of the Compositions of the Invention

The procedure adopted utilizes a column switching techniques similar to the one described above for determination of related substances. The analytical column, guard column, flow rate, detection wavelength were all identical to that described previously. The secondary pump flow rate is changed. Additionally, in order to use isocratic conditions for chromatography, the mobile phase is maintained at 55:45 in 0.1% phosphoric acid and acetonitrile. The same mobile phase was used for reverse flushing of the guard column.

Thus the accumulation of degradants can provide useful information about the shelf-life stability at room temperature. In order to be able to predict the shelf life, the individual degradants and the total percent of all degradants were monitored using the HPLC analytical procedure outlined above. To obtain relative concentrations of the low levels of impurities a surrogate paclitaxel standard at 0.5% of the concentration of paclitaxel in the formulation was used. From a comparison of the relative responses of the individual impurities with respect to the response of paclitaxel under the chromatographic conditions, the percent of each individual degradant as well as the sum of all degradants in the analyte solution was calculated. After storing some of the formulations at a number of temperatures, the degradants formed were monitored using the HPLC procedure. From a plot of percent of either each individual degradant or from a plot of the sum of the degradants formed as a function of temperature, a degradant concentration vs. temperature profile was obtained. From this profile, a mathematical relationship relating shelf life and the extent of degradant formation at 70° C. was developed. Following these procedures, it was determined that the room temperature shelf life Formulation #3 is predicted to be greater than 18 months.

Stability of Paclitaxel in Admixture Solutions

The maintenance of the drug after dilution into solutions useful for intravenous administration, for example, 0.9% sodium chloride (normal saline or NS) or 5% dextrose in water for injection (D5W), so-called admixture solutions, is important. Paclitaxel is poorly soluble in aqueous media and the inability to keep the drug in solution has been suggested (W. C. Rose, *Anticancer Drugs*, 3, 311 (1992)) to explain an observed decrease in the bioavailability of paclitaxel in some solvents.

An admixture solution of Example 2 (6 mg paclitaxel/mL) was prepared by diluting with NS to a paclitaxel concentration of 1.2 mg/mL. The stability of this admixture solution was monitored visually for the formation of precipitates. Surprisingly, this solution did not show any precipitation over a 39 day period. On the other hand, an admixture prepared from a paclitaxel formulation of a 50:50 mixture of solutol:dehydrated ethanol showed visible precipitation after only four days.

An admixture of the compositions in Table 2 was prepared in NS at a concentration of approximately 0.3 mg paclitaxel/mL and the potency monitored as a function of time. The results clearly show that depending on the composition, the admixture stability can be increased from a minimum of 2 days to 6 days (see Table 3). The stability of the admixtures of the present invention can be compared to the currently marketed product, TAXOL (Bristol-Myers Squibb Company) for which the product labeling asserts an admixture stability of 27 hours at room temperature. On the other hand, D. A. Williams and A. Naik, *J. Infusional Chemotherapy*, 4, 140–142 (1994), demonstrated admixture stability of four days at paclitaxel concentrations of 0.1 and 1.0 mg/mL and Xu, L. A. Trissel, J. F. Martinez, *Am. J Hosp. Pharm.*, 51 3058 (1994) disclose at least three day stability at concentrations of 0.03 and 0.6 mg/mL respectively.

TABLE 3

| Composition | 0 hrs | 24 hrs | 48 hrs. | 72 hrs. | 96 hrs. | 6 days |
|---|---|---|---|---|---|---|
| 3 | n.d. | 0.284 | 0.285 | 0.283 | 0.281 | 0.277 |
| 3a | n.d. | 0.280 | 0.278 | 0.280 | 0.281 | 0.279 |
| 3b | n.d. | 0.279 | 0.279 | 0.280 | 0.282 | 0.281 |
| 3c | 0.280 | n.d. | 0.286 | | | |
| 4a | 0.282 | n.d. | 0.286 | | | |
| 4b | 0.282 | n.d. | 0.283 | | | |
| 4c | n.d. | 0.280 | 0.278 | 0.275 | 0.275 | | n.d. = not determined

We claim:

1. A pharmaceutical composition comprising:
   paclitaxel,
   acid,
   water,
   alcohol,
   a polyglycol ester of 12-hydroxystearic acid and polyethylene glycol, and one or more organic solvents.

2. The composition of claim 1 wherein the organic solvent is selected from mono-, di-, or triacetin, mono-, di, or triglyceryl esters of glycerin, mono-, di- or triglycerides, PEG esters, polyvinylpyrrolidone, polysorbate, and pluronic acid.

3. The composition of claim 2 wherein the organic solvent is triacetin and glycerin.

4. The composition of claim 1 wherein the alcohol is selected from ethanol and benzyl alcohol.

5. The composition of claim 4 wherein the alcohol is ethanol.

6. The composition of claim 1 wherein the acid is selected from carboxylic, sulfonic, and mineral acids.

7. The composition of claim 5 wherein the acid is anhydrous citric acid.

8. A pharmaceutical composition comprising:

paclitaxel in the range of about 0.3% to about 0.8% (w/w), anhydrous acid in the range of about 0.2% to about 0.5% (w/w), alcohol in the range of about 10% to about 50% (w/w), water in the range of about 0% to about 25% (w/w), a polyglycol ester of 12-hydroxystearic acid and polyethylene glycol in the range of about 40% to about 50% (w/w), and one or more organic solvents, wherein the total percent of the organic solvents is in the range of about 5% to about 22% (w/w).

9. The composition of claim 8 comprising:

about 0.5% to about 0.7% paclitaxel;

about 0.25% to about 0.35% anhydrous citric acid;

about 14% to about 16% dehydrated ethanol;

about 8% to about 10% water;

about 45% to about 55% Solutol;

about 8% to about 10% triacetin; and about 18% to about 20% glycerol.

10. The composition of claim 9 comprising:

0.57% paclitaxel;

0.27% anhydrous citric acid;

15.1% dehydrated ethanol;

8.9% water;

47.3% Solutol;

9.1% triacetin; and 19.1% glycerol.

11. The composition of claim 1 which is sterilized by terminal sterilization.

12. The composition of claim 8 which is sterilized by terminal sterilization.

13. An admixture comprising the composition of claim 1 and a solution selected from normal saline and D5W.

14. The admixture of claim 13 wherein the solution is normal saline.

15. An admixture comprising the composition of claim 8 and a solution selected from normal saline and D5W.

16. The admixture of claim 15 wherein the solution is normal saline.

* * * * *

UNITED STATES PATENT AND TRADEMARK OFFICE
CERTIFICATE OF CORRECTION

PATENT NO. : 5,922,754

DATED : July 13, 1999

INVENTOR(S) : Mark K. Burchett, et al.

It is certified that error appears in the above-identified patent and that said Letters Patent is hereby corrected as shown below:

On the title page, Item [56] References Cited:

| | | | | | |
|---|---|---|---|---|---|
| 5,616,330 | 04/01/97 | Kaufman, et al. | 424 | 400 | 07/19/94 |
| 5,407,683 | 04/18/95 | Shively | 424 | 439 | 10/01/92 |
| 5,438,072 | 08/01/95 | Bobee et al. | 514 | 449 | 11/22/93 |
| 5,591,715 | 01/07/97 | Coon et al. | 514 | 10 | 06/07/95 |
| 5,776,891 | 07/07/98 | Coon et al. | 514 | 10 | 06/07/95 |
| 5,602,112 | 02/11/97 | Rubinfeld | 514 | 58 | 08/26/94 |

Signed and Sealed this

Nineteenth Day of September, 2000

Attest:

Q. TODD DICKINSON

*Attesting Officer*     *Director of Patents and Trademarks*